United States Patent [19]

Walker

[11] Patent Number: 4,644,010
[45] Date of Patent: Feb. 17, 1987

[54] CERTAIN β-OXO-α-CARBAMOYLPYRROLEPROPIONITRILES

[75] Inventor: Gordon N. Walker, Morristown, N.J.

[73] Assignee: Ciba-Geigy Corporation, Ardsley, N.Y.

[21] Appl. No.: 827,482

[22] Filed: Feb. 5, 1986

Related U.S. Application Data

[63] Continuation of Ser. No. 658,739, Oct. 9, 1984, abandoned, and a continuation-in-part of Ser. No. 426,425, Sep. 28, 1982, abandoned.

[30] Foreign Application Priority Data

Mar. 27, 1984 [ZA] South Africa .................. 84/2238

[51] Int. Cl.$^4$ .................. A61K 31/40; C07D 207/323
[52] U.S. Cl. .................. 514/423; 548/403; 548/540
[58] Field of Search .................. 548/540, 533, 536, 403; 514/423, 427

[56] References Cited

U.S. PATENT DOCUMENTS 4,061,767 12/1977 Ertel et al. .................. 424/282
4,256,759 3/1981 Walker .................. 548/248 X
4,435,407 3/1984 Walker .................. 544/238 X

FOREIGN PATENT DOCUMENTS 3334780A 3/1984 Fed. Rep. of Germany.

OTHER PUBLICATIONS

Dains; J. A. C. S., 35, (1913), pp. 959–970.
Jones; Advances in Heterocyclic Chemistry, 11, pp. 383–472, (1970).

Primary Examiner—Joseph Paul Brust
Attorney, Agent, or Firm—Norbert Gruenfeld

[57] ABSTRACT

1-Unsubstituted β-oxo-α-(phenylcarbamoyl)-β-pyrrolylpropionitriles, e.g. those of the formula

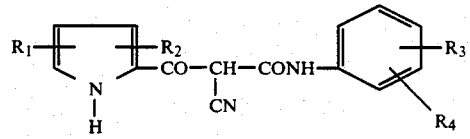

wherein $R_1$ and $R_2$=H or alkyl, and $R_3$ and $R_4$=H, alkyl, alkoxy, OH, halogen or $CF_3$, are analgesic, and antiarthritic agents. Their synthesis, pharmaceutical compositions thereof, and methods of treatment utilizing such compounds are included.

17 Claims, No Drawings

CERTAIN β-OXO-α-CARBAMOYLPYRROLEPROPIONITRILES

This is a continuation of application Ser. No. 658,739 filed Oct. 9, 1984, now abandoned, which is a continuation-in-part of application Ser. No. 426,425 filed Sept. 28, 1982, now abandoned.

BACKGROUND OF THE INVENTION

The inventor's U.S. Pat. No. 4,256,759 is directed to the antiinflammatory and antiarthritic β-oxo-α-(optionally substituted phenylcarbamoyl)-pyrrolepropionitriles substituted at the 1-position of the pyrrole ring by lower alkyl and phenyl lower alkyl. The prior published literature disclosed anilides of α-acetylcyanoacetic acid described in U.S. Pat. No. 4,061,767 and J. Am. Chem. Soc. 35, 959 (1913), as well as anilides of α-benzoylcyanoacetic acid as described in the last said reference.

SUMMARY OF THE INVENTION

The present invention is concerned with α-(optionally substituted phenylcarbamoyl)pyrrolepropionitriles unsubstituted at the 1-position of the pyrrole ring of formula I below representing novel antiinflammatory, antirheumatic agents also having immunomodulating properties indicative of potential disease modifying effects. The compounds of formula I also inhibit cartilage matrix degradation and are analgesic (antinociceptive) agents useful for the alleviation of pain.

The foregoing attributes render the carbamoylpyrrolepropionitriles of this invention useful, when administered alone or in combination, to mammals, e.g. for the treatment of arthritic and rheumatic diseases, such as rheumatoid arthritis and osteoarthritis. They are also useful for the treatment or alleviation of pain in mammals suffering therefrom.

In view of the biological activity of the said compounds that is indicative of their ability to restore depressed cellular mediated immunity, the compounds of this invention may also be useful for the treatment of systemic lupus erythematosus, multiple sclerosis and the like where a defect of the said immune response is suspected.

DETAILED DISCLOSURE OF THE INVENTION

The invention relates to the novel compounds of formula I useful as antirheumatic agents, processes for preparing same, pharmaceutical compositions comprising said compounds, and methods of treating, e.g. rheumatoid arthritis, osteoarthritis, and pain by administration of said compounds and compositions to mammals.

Particularly the invention relates to compounds of the formula I or tautomers thereof

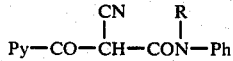
(I)

wherein Py is 2- or 3-pyrrolyl unsubstituted at the 1-position and optionally substituted at one or more of the remaining three positions by lower alkyl and/or by carboxy or lower carbalkoxy and/or by halogen; R is hydrogen or lower alkyl; and Ph is phenyl, unsubstituted or substituted by one to three identical or different members selected from lower alkyl, lower alkoxy, lower alkylthio, lower alkylsulfinyl, lower alkylsulfonyl, hydroxy, halogen, trifluoromethyl, nitro, amino and lower alkanoylamino; pharmaceutically acceptable salts thereof; the lower alkyl enol ethers thereof; or the lower alkanoyl enol esters thereof.

More particularly the invention relates to compounds of formula I, or tautomers thereof, wherein Py represents 2- or 3-pyrrolyl unsubstituted at the 1-position and unsubstituted or substituted at one or more of the remaining three positions by one to three lower alkyl or halogen, by one carboxy or one lower carbalkoxy, or by one or two lower alkyl or halogen in addition to one carboxy or one lower carbalkoxy; R is hydrogen or lower alkyl; Ph is phenyl unsubstituted or substituted by one or two identical or different members selected from lower alkyl, lower alkoxy, lower alkylthio, hydroxy, halogen, nitro, amino and lower alkanoylamino; the pharmaceutically acceptable salts thereof; the lower alkyl enol ethers thereof; or the lower alkanoyl enol esters thereof.

Preferred are compounds of formula I or tautomers thereof wherein Py represents 2-pyrrolyl unsubstituted or substituted at one or more of the 3,4 and 5-positions by one to three lower alkyl groups or by one or two lower alkyl groups in addition to one carboxy or one lower carboalkoxy group at the 3 or 4 positions; Ph is phenyl unsubstituted or substituted by one or two identical or different members selected from lower alkyl, halogen, trifluoromethyl, lower alkylthio, hydroxy and lower alkoxy; pharmaceutically acceptable salts thereof; the lower alkyl enol ethers thereof; or the lower alkanoyl enol esters thereof.

Particularly preferred are the compounds of formula II, or tautomers thereof,

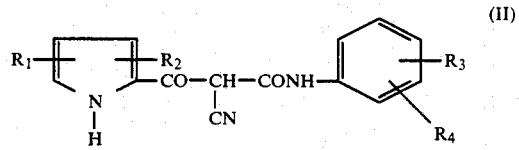
(II)

wherein each of $R_1$ and $R_2$ is independently hydrogen or lower alkyl; and each of $R_3$ and $R_4$ is independently hydrogen, lower alkyl, lower alkoxy, hydroxy, halogen or trifluoromethyl; or a pharmaceutically acceptable salt thereof.

Further preferred are the compounds of formula II wherein each of $R_1$ and $R_2$ is hydrogen; each of $R_3$ and $R_4$ is independently hydrogen, alkyl with up to 4 carbon atoms, fluoro, chloro or trifluoromethyl; or a pharmaceutically acceptable salt thereof.

Highly preferred are the compounds of Formula II, wherein each of $R_1$ and $R_2$ is hydrogen; and each of $R_3$ and $R_4$ is independently hydrogen, methyl, methoxy, fluoro, chloro or trifluoromethyl; or the sodium, potassium, calcium, triethylammonium or tris-(hydroxyethyl)ammonium salt thereof.

Most preferred are the compounds of formula II wherein each of $R_1$ and $R_2$ is hydrogen; each of $R_3$ and $R_4$ is independently hydrogen, fluoro or chloro; or a pharmaceutically acceptable salt thereof.

Particularly preferred are the said compounds of formula II wherein at least one of $R_3$ and $R_4$ is different from hydrogen and is preferably located at the para position of the phenyl ring.

The general definitions used herein have the following meaning within the scope of the present invention.

The term "lower" referred to above and hereinafter in connection with organic radicals or compounds respectively defines such with up to and including 7, preferably up to and including 4 and advantageously one or two carbon atoms.

A lower alkyl group preferably contains 1–4 carbon atoms and represents for example ethyl, propyl, butyl or advantageously methyl.

A lower alkoxy group preferably contains 1–4 carbon atoms and represents for example ethoxy, propoxy, isopropoxy or advantageously methoxy; a lower alkylthio group preferably contains 1–4 carbon atoms and represents advantageously methylthio or ethylthio; a lower alkylsulfinyl group preferably contains 1–4 carbon atoms and represents advantageously methylsulfinyl or ethylsulfinyl; a lower alkylsulfonyl group preferably contains 1–4 carbon atoms and represents advantageously methylsulfonyl or ethylsulfonyl.

Halogen preferably represents chloro or fluoro but may also be bromo or iodo.

Lower alkanoylamino represents preferably acetylamino or propionylamino.

A lower carbalkoxy group represents preferably carboethoxy or carbomethoxy.

Tautomers of the compounds of formula I may be represented by the corresponding enol structure of formula Ia,

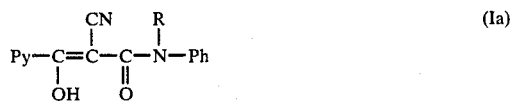

(Ia)

wherein Py, R and Ph have a meaning as previously defined for compounds of formula I, and are in equilibrium therewith.

The compounds of formula I, being in equilibrium with their respective tautomers, have acidic properties and form, as derivatives of the enolic tautomeric structure of formula Ia, lower alkyl enol ethers, lower alkanoyl enol esters, or salts thereof. Salts formed with pharmaceutically acceptable bases, such as alkali metal, alkaline earth metal, copper or zinc hydroxides, ammonia, mono-, di- or tri-lower (alkyl or hydroxyalkyl)-amines, monocyclic amines or alkylenediamines, are e.g. sodium, potassium, magnesium, ammonium, mono-, di- or tri-(methyl, ethyl or hydroxyethyl)-ammonium, pyrrolidinium, ethylenediammonium or morpholinium salts; or various hydrates thereof.

The compounds of the invention exhibit valuable pharmacological properties, primarily antiinflammatory, analgesic (antinociceptive), antirheumatic, immunopotentiating and antiarthritic activity. These can be demonstrated by in-vitro or in-vivo tests, using for the latter advantageously mammals, such as rats, mice, guinea pigs or dogs, as test objects. The compounds of the invention can be administered to the animals either enterally, preferably orally, parenterally, e.g. subcutaneously or intravenously, or topically, for example, in the form of aqueous or oily solutions or starchy suspensions. The applied dosage may range between about 0.1 and 100 mg/kg/day, preferably between about 1 and 50 mg/kg/day, advantageously between about 5 and 25 mg/kg/day. The tests chosen are among the classical assay methods for said activities, such as the carrageenin paw-edema, or adjuvant arthritis tests in rats, the canine synovitis or ultraviolet erythema assays, or more recent tests, such as neutral protease inhibition, described in Arthritis Rheum. 17, 47 (1974), or inhibition of leukocyte chemotaxis, described in Ann. N.Y. Acad. Sci., 256, 177 (1975); or decrease of neutrophil adherence, described in Amer. J. Med. 61, 597 (1976); or inhibition of prostaglandin synthetase, described in Biochem. 10, 2372 (1971); or the phenylquinone writhing test in mice described in J. Pharmcol. Exp. Therap. 125, 237 (1959).

Immunopotentiating effects are determined in BCG-immunized animals in vitro and in vivo.

Enhancement of cell-mediated immunity is determined in vitro as follows by measurement of increased chemotaxis of monocytes.

Male Charles River rats, weighing 250–300 g are immunized by intradermal injections of 0.1 ml Bacillus Calmette Guerin (BCG) vaccine. One week later, the animals are injected with 10 ml of a sterile 2% rice starch solution intraperitoneally, to induce the accumulation of macrophages. On day 11 after immunization, the animals are sacrificed and peritoneal macrophages collected with 20 ml of Gey's balanced salt solution containing heparin (25 units/ml). The harvested cells are centrifuged at 1000 RPM for 10 minutes, washed with 50 ml more of Gey's solution at the same speed and time, and then they are resuspended in Gey's solution containing 0.1% human serum albumin to yield a concentration of $2 \times 10^6$ cells/ml.

The test substances are dissolved in dimethylacetamide to yield a $1 \times 10^{-2}$M solution. Subsequent dilutions are made with Gey's solution, and they are finally added to the above cell suspension to yield the appropriate final concentrations of $10^{-4}$, $10^{-5}$, $10^{-6}$ and $10^{-7}$M. Said substances remain with the cells after the suspensions are distributed over the upper compartment of the modified Boyden chemotaxis chambers. E. coli lipopolysaccharide (Difco) activated rat serum (1/10 dilution at pH=7.1) is used as the chemotactic agent and placed in the lower compartment of said chambers. The cell compartment of the chamber is separated from the chemotactic solution by a 8 micron pore size cellulose filter membrane, the chambers are set up in triplicate and incubated for 5 hours at 37° C. Cell suspensions alone, without test compound, serve as controls for cell-migration. After incubation, the filters are removed, fixed and stained with Weigert's iron hematoxylin, four fields of the lowermost surface of the filter are examined and microscopically at a magnification of 320. The average of the number of neutrophils counted in those four fields is used as an index of chemotactic activity.

The enhancement of cell-mediated immunity is determined in vivo in the BCG-immunized arthritic rat by measurement of delayed hypersensitivity reaction essentially as described in Current Therapeutic Research 30, S34 (1981).

Charles River male rats weighing 325–400 g are sensitized by intradermal injection into the right hind foot pad with 250 g per animal of Mycobacterium tuberculosis (Difco) emulsified in Freund's incomplete adjuvant. Animals are immunized with 0.1 ml of BCG vaccine intradermally on day 18 after adjuvant injection. Corn starch suspensions of drugs are administered orally. Control animals are dosed with cornstarch vehicle only. All animals are skin-tested with 10 μg PPD intradermally on day 29 to elicit skin reactions. The diameter of the erythema and induration reaction is measured 24 hours after antigen challenge. An increase in the diameter of the erythema is indicative of enhanced cellular immunity.

The carrageenin paw-edema assay for antiinflammatory activity is carried out in rats as follows:

One hour after compounds are administered orally, 0.1 ml of carrageenin (1%) is injected into plantar area of one hind paw. Difference of swelling is measured between contralateral and injected paw by means of mercury displacement at designated times.

The established adjuvant arthritis test for antiarthritic activity is performed essentially as described in Proc. Soc. Biol. Med. 137, 506 (1971).

The phenyl-p-benzoquinone-induced writhing test for analgesic activity, described in J. Pharmacol. Exp. Therap. 125, 237 (1959) is performed in mice as follows:

Mice previously fasted overnight are treated orally with the test compound dissolved in 0.75% methylcellulose at doses of 1 to 50 mg/kg, or with the vehicle alone, 55 minutes before the induction of the writhing syndrome by i.p. injection of 0.25 ml of a suspension of phenyl-p-benzoquinone (0.03%) in tragacanth (0.4%).

Starting 5 minutes, thereafter, the number of writhing movements provoked by the irritant are counted over an observation period of 10 minutes. The analgesic antinociceptive) $ED_{50}$ of the test compound is the dose which reduces the mean frequency of writhing movements by 50% in comparison to the controls.

Illustrative of the invention, $\beta$-oxo-$\alpha$-(phenylcarbamoyl)-$\beta$-(2-pyrrolyl)-propionitrile of example 1 and $\beta$-oxo-$\alpha$-(4-chlorophenyl)-$\beta$-(2-pyrrolyl)-propionitrile of example 2 both at a dose of 100 mg/kg/p.o. afford protection against carrageenin-induced edema in rats measured 3 hours after administration by 46 and 63% respectively. Similarly, $\beta$-oxo-$\alpha$-(2,4-difluorophenylcarbamoyl)-$\beta$-(2-pyrrolyl)-propionitrile of example 3 at a dose of 25 mg/kg/po affords 33% protection.

Furthermore, the compounds of the invention, e.g. illustrative compounds of Examples 1, 2, 3 and 5 are active in the established adjuvant arthritis test in the rat when administered at a dose ranging from about 5 to 25 mg/kg/p.o.

The compounds of the invention, e.g. the compounds of Examples 1, 2, 3 and 5 are active in the phenyl-p-benzoquinone test for analgesia in the mouse when administered at a dose ranging from about 1 to 30 mg/kg p.o.

Indicative of the immunopotentiating activity of the compounds of this invention, illustrative compounds of examples 1 and 2 exhibit significant activity in the skin test in the BCG-immunized adjuvant arthritic rat at a dose of 25 mg/kg/p.o.

The compounds of the invention are also active in the cartilage-synovium co-culture model of cartilage matrix degradation, indicative of their effectiveness in osteoarthritis. The screen is carried out as follows:

The proteoglycan matrix of bovine nasal septum cartilage is labeled into vitro by incorporation of $^{35}S$ into glycosaminoglycan. Cartilage slices are incubated overnight in a sulfate-free medium containing $^{35}S$-sodium sulfate. $^{35}S$-Labeled cartilage slices are co-cultured with normal synovium explants in multiwell tissue culture plates. After 4 days incubation a 100 $\mu$l aliquot of medium is counted. Cartilage slices are hydrolyzed and a 100 $\mu$l aliquot of cartilage hydrolysate is counted. The percent $^{35}S$ released into the medium is determined and the percent of inhibition of matrix degradation is calculated.

Illustrative of the invention, $\beta$-oxo-$\alpha$-(phenylcarbamoyl)-$\beta$-(2-pyrrolyl) propionitrile of example 1, $\beta$-oxo-$\alpha$-(4-chlorophenylcarbamoyl)-$\beta$-(2-pyrrolyl)-propionitrile of example 2 and $\beta$-oxo-$\alpha$-(2,4-difluorophenylcarbamoyl)-$\beta$-(2-pyrrolyl)-propionitrile of example 3 inhibit cartilage matrix degradation in vitro at a concentration range of about $10^{-7}M$ to $10^{-5}M$.

The aforementioned advantageous properties render the compounds of the invention useful as antiinflammatory, analgesic, antiarthritic and immunopotentiating agents especially for the treatment and amelioration of e.g. pain and inflammatory disorders, such as rheumatoid arthritis and osteoarthritis in mammals, including man.

The compounds of formula I can be prepared by synthetic procedures which are per se known to those skilled in the art, specifically (a) condensing together the compounds of the formulae

Py—COCH$_2$—CN         (III)

and

pH—N=C=O              (IV)

and, if desired, N-substituting a resulting compound with a reactive ester of ROH, wherein Py, Ph and R have meaning as previously defined; or (b) removing the group Z from a compound of the formula

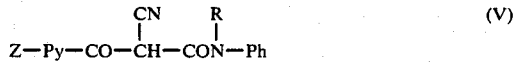

$$Z-Py-CO-\underset{\underset{CN}{|}}{C}H-\underset{\underset{R}{|}}{C}ON-Ph \qquad (V)$$

wherein Py, R and Ph have meaning as described above, and Z is a protecting group on the pyrrole nitrogen, e.g., optionally substituted benzyl, optionally substituted carbobenzyloxy, lower alkanoyl (such as acetyl), trifluoroacetyl, di-lower alkylamino (such as dimethylamino), tetrahydropyranyl, lower alkyloxymethyl (such as methoxymethyl), lower alkoxycarbonyl (such as t-butyloxycarbonyl); or (c) condensing a compound of formula VI, advantageously as a reactive functional derivative thereof,

$$Py-\underset{\underset{CN}{|}}{C}OCH-COOH \qquad (VI)$$

with an amine of the formula R—NH—Ph (VII) wherein Py, R, and Ph are as defined above; or (d) ring opening a compound of the formula VIII

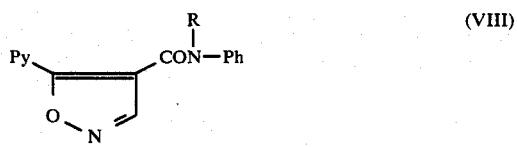

(VIII)

wherein Py, R, Ph having meaning as described; or (e) condensing a compound of formula IX, advantageously a functional derivative thereof, with a compound of formula X

Py—COOH              (IX)

-continued

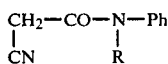  (X)

wherein Py, R, Ph have meaning as described above;

(f) reacting ammonia or salt thereof with a compound of formula XI

  (XI)

wherein R and Ph have the meaning as described above, and Y represents unsubstituted or substituted 2,5-di-(loweralkoxy or halo)-2-tetrahydrofuranyl; optionally (g) converting a resulting compound of formula I into another compound of formula I; and optionally (h) converting any resulting compound of formula I into an addition salt thereof, or liberating the free compound from an addition salt thereof.

The condensation according to processes (a) of the isocyanate of formula IV with the pyrroloylacetonitrile of formula III may be carried out according to U.S. Pat. No. 4,256,759, i.e., in the absence or presence of an inorganic or organic base, such as sodium hydride or triethylamine or in the presence or absence of a polar solvent, such as an ether, e.g. diethyl ether or tetrahydrofuran, and/or an amide or sulfoxide, e.g. dimethylformamide or dimethyl sulfoxide; preferably at a temperature range of 25° to 100° C.; advantageously at elevated temperatures, e.g. at about 150° if no base is used.

The above-preferred process (a) according to the invention is generally performed thus: said nitrile is treated with a slight molar excess of an anhydrous tri-lower alkylamine, preferably triethylamine, and then a molar equivalent of the appropriate phenyl isocyanate (Ph—N=C=O) is added, or a solution thereof in the polar solvents mentioned above, e.g. dimethylsulfoxide or glyme. After stirring for about 2-24 hours at room temperature, the reaction mixture is reduced in volume by evaporation without excessive warming. The residue is treated with an excess of dilute aqueous acid, e.g. 0.1-0.3N hydrochloric acid and the crude products are extracted or collected, washed with water, dried, triturated and/or recrystallized from appropriate solvents, such as lower alkanols, alkanones, dialkyl ethers and/or alkyl alkanoates, e.g. methanol, acetone, diethyl ether and/or ethyl acetate.

The starting materials of formula III and IV are either known or are prepared according to methods well-known to the art, e.g. for compounds of formula III as described in Ber. 113, 3675 (1980), Chem. Abstracts, 29, 2164 and Ber. 55, 2390 (1922).

The compounds of formula III wherein Py represents optionally substituted 2-pyrrolyl as defined above are preferably prepared by condensation of a compound of the formula PyH (with hydrogen at the 2-position) with malononitrile under acidic conditions, preferably in the presence of an anhydrous acid, e.g. hydrogen chloride, in an inert solvent preferably at room temperature. The resulting enamine nitrile salt is then converted by hydrolysis with water to the said compound of formula III.

Process (b) involving the removal of group Z is carried out by methods well-known to the art, e.g. (1) by hydrogenolysis when Z represents optionally substituted benzyl or carbobenzyloxy, e.g. with hydrogen in the presence of a hydrogenation catalyst; (2) by hydrolysis, preferably in the presence of e.g. a mineral acid or by ion exchange according to J. Am. Chem. Soc. 101, 6789 (1979), when Z represents optionally substituted carbobenzyloxy, lower alkanoyl, trifluroacetyl, lower alkoxycarbonyl, lower alkoxymethyl, or tetrahydropyranyl; (3) by oxidative cleavage, when Z represents dialkylamino, with chromium (II) acetate according to J. Org. Chem. 46, 3760 (1981).

The starting materials of formula V are prepared by e.g. condensing an acid of formula XII,

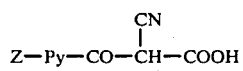  (XII)

preferably as a reactive functional derivative thereof, wherein Z and Py are as defined above, with an amine of the formula R—NH—Ph (VII).

The condensation is carried out according to U.S. Pat. No. 4,256,759 advantageously between room temperature and about 150°, either with equivalent amounts of the reactants (when a reactive ester is used), or with an excess of the amine, or in the presence of another base, such as a tertiary amine, e.g. a tri-lower alkylamine or pyridine (when a halide or anhydride is used) in order to neutralize the generated acid. The lower alkanol, generated in the reaction with said esters, is preferably distilled off together with a diluent, such as an aromatic hydrocarbon, e.g. benzene, toluene or xylene. The condensation using a free carboxylic acid is preferably carried out in the presence of a condensing agent, e.g. a disubstituted carbodiimide, such as dicyclohexylcarbodiimide, or 1,1'-carbonyldiimidazole.

Said starting materials of formula V may also be prepared according to other methods as described in U.S. Pat. No. 4,256,759.

The condensation of process (c) is carried out similarly to methods described above for the preparation of compounds of formula V.

The starting materials of formula VI are prepared e.g. by reacting a compound of formula III with a derivative of carbonic acid, e.g. ethyl chloroformate to give e.g. the corresponding ethyl ester of a compound of formula VI, which in turn may be converted to a compound of formula VI, or a reactive functional derivative thereof, by conventional means.

The ring opening reaction according to process (d), a reaction known to the art as described in J. Am. Chem. Soc. 35, 959 (1913), is carried out in the presence of strong inorganic or organic bases, e.g. alkali metal hydroxides or tri-lower alkyl-aralkylammonium hydroxides, e.g. trimethylbenzylammonium hydroxide.

The isoxazole starting materials of formula VIII are also prepared by procedures well-known to the art, e.g. as disclosed in J. Am. Chem. Soc. 35, 959 (1913).

The condensation according to process (e), when the starting material is preferably a reactive functional derivative of a compound of formula IX, is advantageously performed in the presence of metallizing agents such as alkali metals, metal alkoxides or hydrides, e.g. sodium hydride, potassium t-butoxide, thallous ethoxide, or under phase transfer conditions, in polar solvents, e.g. 1,2-dimethoxyethane, dimethylformamide, dimethyl sulfoxide at temperatures ranging from about 0° to 100°, preferably at 25° to 50°.

Reactive functional derivatives of the carboxylic acids of formulae VI, IX and XII are for example anhydrides especially mixed anhydrides, acid halides, the acid azide, lower alkyl esters and activated esters thereof. Mixed anhydrides are preferably such from pivalic acid, or a lower alkyl (ethyl, isobutyl) hemiester of carbonic acid; acid halides are for example chlorides or bromides; activated esters are for example succinimido, phthalimido or 4-nitrophenyl esters; lower alkyl esters are for example the methyl or ethyl esters.

The condensation of a free carboxylic acid of formula VI, IX and XII with a compound of formula VII or X, according to the above processes, may be carried out in the presence of a condensing agent, e.g. diethyl phosphorocyanidate, in the presence of a base, e.g. triethylamine, in an inert polar solvent, e.g. dimethylformamide or methylene chloride.

The reaction according to process (f) preferably involves the reaction of ammonium acetate with a compound of formula XIa

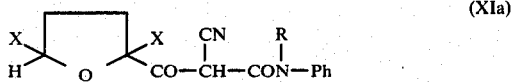
(XIa)

wherein R and Ph have the meaning as previously described above, X represents methoxy, ethoxy or chloro, advantageously carried out in glacial acetic acid at elevated temperature, according to methodology well-known in the art, e.g. as described in Acta Chimica Scandinavia 6, 862–874 (1952).

The compounds of the invention, so obtained, can be converted into each other according to methods known per se. Thus, for example, resulting compounds (as enols) can be etherified, e.g. with lower diazoalkanes, or esterified, e.g. with lower alkanoic acid anhydrides; or converted into salts with said pharmaceutically acceptable bases, e.g. an aqueous alkali metal hydroxide, advantageously in the presence of an ethereal or alcoholic solvent, such as a lower alkanol. From the solutions of the latter, the salts may be precipitated with said ethers, e.g. diethyl ether or tetrahydrofuran, at moderate temperatures, e.g. below 100°. Resulting salts may be converted into the free compounds by treatment with acids or bases. These or other salts can also be used for purification of the compounds obtained. In view of the close relationship between the free compounds and the compounds in the form of their salts, whenever a compound is referred to in this context, a corresponding salt is also intended provided such is possible or appropriate.

The starting materials used are known, or if new, can be prepared according to the methods used in the references cited or as illustrated by the examples herein.

The above reactions are otherwise carried out according to standard methods, in the presence or absence of diluents, preferably such as are inert to the reagents and are solvents thereof, of catalysts, condensing or neutralization agents and/or inert atmospheres, at low temperatures, room temperature or elevated temperatures, at atmospheric or superatmospheric pressure.

The invention also comprises any modification of the above processes, wherein a compound resulting as an intermediate at any stage thereof, is used as starting material and the remaining steps are carried out, or the process is discontinued at any stage thereof, or in which the starting material is formed under the reaction conditions or is used in the form of its salts or reactive derivatives, preferably alkali metal or trialkylammonium salts of said enols. In said processes of the invention those starting materials are advantageously selected, which yield the above-described preferred embodiments of the invention.

The invention also relates to novel intermediates and processes for their manufacture.

Depending on the choice of starting materials and methods, the new compounds may be in the form of one isomer, tautomer or mixtures thereof, provided such are possible.

The compounds, including their salts, can also be obtained in the form of their hydrates, or include other solvents used for the crystallization.

The pharmaceutical compositions according to the invention are those suitable for enteral, such as oral or rectal, and parenteral administration to mammals, including man, for the alleviation and treatment of pain and inflammatory, arthritic and immunologically mediated diseases such as osteoarthritis and rheumatoid arthritis comprising an effective amount of a pharmacologically active compound of formula I, or a pharmaceutically acceptable salt thereof, alone or in combination with one or more pharmaceutically acceptable carriers.

The pharmacologically active compounds of the invention are useful in the manufacture of pharmaceutical compositions containing an effective amount thereof in conjunction or admixture with excipients suitable for either enteral, parenteral or topical application. Preferred are tablets and gelatin capsules comprising the active ingredient together with (a) diluents, e.g. lactose, dextrose, sucrose, mannitol, sorbitol, cellulose and/or glycine; (b) lubricants, e.g. silica, talcum, stearic acid, its magnesium or calcium salt and/or polyethyleneglycol; for tablets also (c) binders, e.g. magnesium aluminum silicate, starch paste, gelatin, tragacanth, methyl cellulose, sodium carboxymethylcellulose and/or polyvinylpyrrolidone; if desired, (d) disintegrants, e.g. starches, agar, alginic acid or its sodium salt, or effervescent mixtures; and/or (e) absorbents, colorants, flavors and sweeteners. Injectable compositions are preferably aqueous isotonic solutions or suspensions, and suppositories or topical lotions are advantageously made from fatty emulsions or suspensions. They may be sterilized and/or contain adjuvants, such as preserving, stabilizing, wetting or emulsifying agents, solution promoters, salts for regulating the osmotic pressure and/or buffers. Said pharmaceutical compositions may also contain other therapeutically valuable substances. They are prepared according to conventional mixing, granulating or coating methods respectively and contain about 0.1 to 75%, preferably about 1 to 50%, of the active ingredient.

A unit dosage for a mammal of about 50 to 70 kg may contain between about 10 to 200 mg of the active ingredient.

The following examples are intended to illustrate the invention and are not to be construed as being limitations thereon. Temperatures throughout are given in degrees Centigrade and all parts wherever given are parts by weight. If not otherwise stated, evaporations are carried out under reduced pressure, preferably between about 15 and 100 mm Hg.

EXAMPLE 1

A solution of 3.1 g of 2-pyrroloylacetonitrile in 25 ml of glyme (ethylene glycol dimethyl ether) and 2.7 g of anhydrous triethylamine is treated with 3.0 g of phenyl isocyanate. After the moderately exothermic reaction, the mixture is let stand overnight. Most of the solvent is evaporated and the residue is treated with water and 12 ml of 10% NaOH solution. The aqueous, alkaline solution is washed with ethyl acetate and acidified with 6N HCl. The product is collected, washed with water, dried and recrystallized from ethanol, to give β-oxo-α-(phenylcarbamoyl)-β-(2-pyrrolyl)-propionitrile, m.p. 207°–209°, the compound of formula II, wherein $R_1$ to $R_4$ are hydrogen.

The starting material is prepared as follows:

Into an ice-chilled solution of 30 g of pyrrole and 30 g of malononitrile in 800 ml of dry ether is passed by HCl for 20 minutes. After standing several hours the suspension is filtered to give 65 g of orange-brown, water-soluble solid. The solution of 50 g of this intermediate (the enamine nitrile hydrochloride) in 600 ml of water is covered with 400 ml of ethyl acetate and stirred for 2½ hours at room temperature. The organic layer is separated, dried (MgSO₄) and evaporated to give crystals, m.p. 77°–9°; additional product is obtained by warming the aqueous layer on steam cone for ½ hour and extracting with ethyl acetate. Recrystallization from water gives 2-pyrroloylacetonitrile, m.p. 79°–81°.

EXAMPLE 2

To the solution of 6.7 g of 2-pyrroloylacetonitrile in 25 ml of glyme and 5.5 g of Et₃N is added a solution of 8.6 g of 4-chlorophenyl isocyanate in 25 ml of glyme. After the exothermic reaction, the mixture is let stand overnight. Part of the solvent is evaporated and the cooled residue is poured into a solution of 10 ml of 6N HCl in 250 ml of water. After the addition of some methanol, the crude material is collected. It is dissolved in dilute NaOH solution, the solution is treated with charcoal, filtered, and acidified with 6N HCl. The reprecipitated product is collected, washed with water, and triturated with methanol to give solid, m.p. 219°–221°. Recrystallization from methanol gives β-oxo-α-(4-chlorophenyl carbamoyl)-β-(2-pyrrolyl)propionitrile, m.p. 223°–5°.

EXAMPLE 3

Reaction of 2.4 g of 2-pyrroloylacetonitrile with 3.1 g of 2,4-difluorophenyl isocyanate in the presence of 2.0 g Et₃N in 25 ml of glyme and isolation similarly to the preceding examples, followed by trituration with and recrystallization from ethanol gives β-oxo-α-(2,4-difluorophenylcarbamoyl)-β-(2-pyrrolyl)-propionitrile, m.p. 169°–171°.

EXAMPLE 4

Reaction of 2.0 g of 2-pyrroloylacetonitrile with 3.0 g of 3-(trifluoromethyl)-phenyl isocyanate in the presence of 1.8 g of Et₃N in 25 ml of glyme similarly to the previous examples and recrystallization of the crude product from methanol gives β-oxo-α-(3-trifluoromethylphenylcarbamoyl)-β-(2-pyrrolyl)-propionitrile, m.p. 210°–212°.

EXAMPLE 5

Reaction of 2.4 g of 2-pyrroloylacetonitrile with 2.5 g of 4-fluorophenyl isocyanate in the presence of 2.2 g of Et₃N in 25 ml of glyme, similarly to preceding examples, reprecipitation from dilute NaOH solution with HCl, and recrystallization from methanol, gives β-oxo-α-(4-fluorohenylcarbamoyl)-β-(2-pyrrolyl)-propionitrile, m.p. 233°–4°.

EXAMPLE 6

Reaction of 2.7 g of 2-pyrroloylacetonitrile with 3.8 g of 3-chloro-4-fluorophenyl isocyanate in the presence of 2.4 g of Et₃N in 25 ml of glyme and workup similarly to the preceding examples gives after recrystallization from ethyl acetate, β-oxo-α-(3-chloro-4-fluorophenylcarbamoyl)-β-(2-pyrrolyl)-propionitrile, m.p. 257°–8° dec.

EXAMPLE 7

A solution of 2.1 g of 2-pyrroloylacetonitrile in 15 ml of glyme and 1.8 g of Et₃N is treated with a solution of 3 g of 2,4-dichlorophenyl isocyanate in 15 ml of glyme similarly to the preceding examples. Mildly exothermic reaction results in formation of a thick suspension of crystals. After standing overnight, dilution with dry ether and filtration gives the triethylamine salt of β-oxo-α-(2,4-dichlorophenylcarbamoyl)-β-(2-pyrrolyl)-propionitrile, m.p. 180°–2° dec., in form of the enol structure as represented by formula Ia, wherein Py is 2-pyrrolyl, R is hydrogen and Ph is 2,4-dichlorophenyl.

A solution of the above triethylamine salt in methanol is added to a solution of 4 ml of 6N HCl in 250 ml of water. The free enolic product is collected, washed with water and triturated with methanol to give crystals, m.p. 219°–221°. Recrystallization from ethyl acetate gives β-oxo-α-(2,4-dichlorophenylcarbamoyl)-β-(2-pyrrolyl)-propionitrile, m.p. 222°–3°.

EXAMPLE 8

A mixture of 1.1 g of β-oxo-α-ethoxycarbonyl-β-(2-pyrrolyl)-propionitrile, 1.5 g of 4-fluoroaniline and 60 ml of xylene, is refluxed for 4½ hours. After standing and cooling to room temperature overnight, the solution is filtered, evaporated and the residue is purified to yield β-oxo-α-(4-fluorophenyl carbamoyl)-β-(2-pyrrolyl)-propionitrile of example 5.

The starting material is prepared as follows:

(a) 2-Pyrroloylacetonitrile is treated in the presence of triethylamine in ethylene glycol dimethyl ether at 50° overnight with ethyl chloroformate, and the product is purified to give β-oxo-α-ethoxycarbonyl-β-2-(pyrrolyl)-propionitrile.

(b) A solution of 2.2 g of pyrrole-2-carboxylic acid, 8.4 ml of anhydrous triethylamine and 2.1 ml of ethyl cyanoacetate in dimethylformamide is treated with 2.9 ml of diethyl phosphorocyanidate at room temperature. After stirring for 80 minutes at room temperature, the reaction mixture is cooled in an ice bath, treated with about 50 ml of water and acidified with 6N hydrochloric acid. The crude precipitate is collected, washed with water, dried and recrystallized from ether to yield β-oxo-α-ethoxycarbonyl-β-(2-pyrrolyl)-propionitrile, m.p. 138°–9°.

EXAMPLE 9

By procedures analogous to those described in the preceding examples the following examples of formula I can be prepared.

| No. | Py | R | Ph |
|---|---|---|---|
| 9/1 | 2-pyrrolyl | H | 4-methoxyphenyl |
| 9/2 | 2-pyrroyl | H | 4-methylthiophenyl |
| 9/3 | 2-pyrroyl | H | 4-hydroxyphenyl |

-continued

| No. | Py | R | Ph |
|---|---|---|---|
| 9/4 | 2,5-dimethyl-3-pyrrolyl | H | 4-chlorophenyl |
| 9/5 | 3,5-dimethyl-2-pyrrolyl | H | 2,4-difluorophenyl |
| 9/6 | 3,5-dimethyl-4-carbo-ethyoxy-2-pyrrolyl | H | 4-chlorophenyl |
| 9/7 | 2-pyrrolyl | H | 4-trifluoromethylphenyl |
| 9/8 | 2-pyrrolyl | H | 4-tolyl |
| 9/9 | 2-pyrrolyl | $CH_3$ | phenyl |

The pyrrole starting materials for examples 9/4, 9/5 and 9/6 are described in Ber. 113, 3675 (1980), Chem. Abstr. 29, 2164, and Ber. 55, 2390 (1922) respectively.

EXAMPLE 10

Treatment of β-oxo-α-(phenylcarbamoyl)-β-(2-pyrrolyl)-propionitrile with an equivalent amount of a concentrated aqueous or alcoholic solution of sodium, potassium or calcium hydroxide or ethoxide and evaporating to dryness, will yield the corresponding sodium, potassium or calcium salt of the compound in tautomeric form of formula Ia, wherein Py is 2-pyrrolyl, Ph is phenyl and R is hydrogen.

Similarly prepared with an equivalent amount of triethylamine or tri-(hydroxyethyl)-amine are the triethylammonium and tris-(hydroxyethyl)-ammonium salts respectively.

EXAMPLE 11

To 500 ml of ethereal diazomethane, generated from 10.3 g of N-nitroso-N-methylurea with 35 ml of 45% aqueous potassium hydroxide and dried over KOH pellets, are added 3.9 g of β-oxo-α-(phenylcarbamoyl)-β-(2-pyrrolyl)-propionitrile. After the nitrogen evolution ceases, the solution is filtered and evaporated. Purification will yield the corresponding methyl enol ether, i.e. the β-methoxy-α-(phenylcarbamoyl)-β-(2-pyrrolyl)-acrylonitrile.

EXAMPLE 12

(a) to a solution of 1.6 g of α-cyanoacetanilide in 10 ml of dimethylformamide is added 3.4 g of potassium t-butoxide. The stirred cooled suspension is treated with a solution of 1.1 g of pyrrole-2-carboxylic acid and 1.4 ml of diethyl phosphorocyanidate in 6 ml of dimethylformamide. After standing for one half hour, solution is treated with 80 ml of cold water, filtered and acidified with 6N hydrochloric acid. The suspended product is collected, washed with water, dried, and dissolved in ethyl acetate. The ethyl acetate solution is filtered and evaporated to dryness. Recrystallization from ether-ethanol yields β-oxo-α-(phenylcarbamoyl)-β-(2-pyrrolyl)-propionitrile of Example 1.

The starting α-cyanoacetamilide is prepared by condensation of cyanoacetic acid with aniline in acetonitrile in the presence of dicyclohexylcarbodiimide.

(b) Similarly, β-oxo-α-(4-fluorophenylcarbamoyl)-β-(2-pyrrolyl)-propionitrile of Example 5 is obtained using p-fluoroaniline as the starting material.

EXAMPLE 13

Preparation of 1,000 capsules each containing 25 mg of the active ingredient:

Formula

β-Oxo-α-(4-fluorophenylcarbamoyl)-β-(2-pyrrolyl)-propionitrile: 25.0 g
Lactose: 207.0 g
Modified starch: 80.0 g
Magnesium stearate: 3.0 g Procedure All the powders are passed through a screen with openings of 0.6 mm. Then the drug substance is placed in a suitable mixer and mixed first with the magnesium stearate, then with the lactose and starch until homogeneous. No. 2 hard gelatin capsules are filled with 315 mg of said mixture each, using a capsule filling machine.

Analogously capsules are prepared, containing 10–200 mg of the other compounds disclosed and illustrated herein.

EXAMPLE 14

Preparation of 10,000 tablets each containing 100 mg of the active ingredient:

Formula

β-Oxo-α-(2,4-difluorophenylcarbamoyl)-β-(2-pyrrolyl)propionitrile: 1,000.00 g
Lactose: 2,535.00 g
Corn starch: 125.00 g
Polyethylene glycol 6,000: 150.00 g
Talcum powder: 150.00 g
Magnesium stearate: 40.00 g
Purified water: q.s.

Procedure

All the powders are passed through a screen with openings of 0.6 mm. Then the drug substance, lactose, talcum, magnesium stearate and half of the starch are mixed in a suitable mixer. The other half of the starch is suspended in 65 ml of water and the suspension added to the boiling solution of the polyethylene glycol in 260 ml of water. The paste formed is added to the powders, which are granulated, if necessary, with an additional amount of water. The granulate is dried overnight at 35°, broken on a screen with 1.2 mm openings and compressed into tablets, using concave punches uppers bisected.

Analogously tablets are prepared, containing 10–200 mg of one of the other compounds illustrated by the previous examples.

What is claimed is:

1. A compound of the formula $$\text{(II)}$$

[structure showing pyrrole ring with $R_1$, $R_2$ substituents, -CO-CH(CN)-CONH- linker to phenyl ring with $R_3$, $R_4$ substituents, and N-H on pyrrole]

or an enol tautomer thereof wherein each of $R_1$ and $R_2$ is independently hydrogen or lower alkyl of 1 to 4 carbon atoms; and each of $R_3$ and $R_4$ is independently hydrogen, lower alkyl of 1 to 4 carbon atoms, halogen or trifluoromethyl; or a pharmaceutically acceptable alkali metal, alkaline earth metal, copper, zinc, ammonium, or a mono-, di- or tri-$C_1$-$C_4$(alkyl or hydroxyalkyl)-ammonium salt thereof.

2. A compound of claim 1 wherein each of $R_1$ and $R_2$ is hydrogen; each of $R_3$ and $R_4$ is independently hydrogen, alkyl of 1 to 4 carbon atoms, fluoro, chloro or trifluoromethyl; or a pharmaceutically acceptable salt thereof as defined in said claim.

3. A compound of claim 2 wherein each of $R_1$ and $R_2$ is hydrogen; each of $R_3$ and $R_4$ is independently hydrogen, fluoro or chloro; or a pharmaceutically acceptable salt thereof as defined in said claim.

4. A compound of claim 1 being β-oxo-α-(2,4-difluorophenylcarbamoyl)-β-(2-pyrrolyl)-propionitrile, or the sodium, potassium, calcium, triethylammonium or tris-(hydroxyethyl)ammonium salt thereof.

5. A compound of claim 1 being β-oxo-α-(4-chlorophenylcarbamoyl)-β-(2-pyrrolyl)-propionitrile or the sodium, potassium, calcium, triethylammonium or tris-(hydroxyethyl)-ammonium salt thereof.

6. A compound of claim 1 being β-oxo-α-(3-trifluoromethylphenylcarbamoyl)-β-(2-pyrrolyl)-propionitrile or the sodium, potassium, calcium, triethylammonium or tris-(hydroxyethyl)-ammonium salt thereof.

7. A compound of claim 1 being β-oxo-α-(phenylcarbamoyl)-β-(2-pyrrolyl)-propionitrile or the sodium, potassium, calcium, triethylammonium or tris-(hydroxyethyl)ammonium salt thereof.

8. A compound of claim 1 being β-oxo-α-(4-fluorophenylcarbamoyl)-β-(2-pyrrolyl)-proprionitrile or the sodium, potassium, calcium, triethylammonium or tris-(hydroxyethyl)-ammonium salt thereof.

9. An analgesic pharmaceutical composition comprising an analgetically effective amount of a compound of claim 1 in combination with one or more pharmaceutically acceptable carriers.

10. A method of treating pain in a mammal which comprises administering to a mammal in need thereof an effective analgesic amount of a compound of the formula

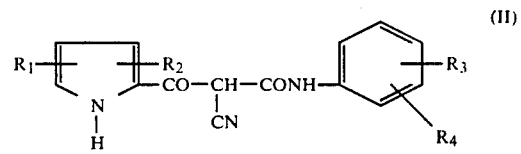

or an enol tautomer thereof wherein each of $R_1$ and $R_2$ is independently hydrogen or lower alkyl of 1 to 4 carbon atoms; and each of $R_3$ and $R_4$ is independently hydrogen, lower alkyl of 1 to 4 carbon atoms, halogen or trifluoromethyl; or of a pharmaceutically acceptable alkali metal, alkaline earth metal, copper, zinc, ammonium, or a mono-, di- or tri-$C_1$-$C_4$-(alkyl or hydroxyalkyl)-ammonium salt thereof; or of a pharmaceutical composition comprising a said compound or a said salt thereof in combination with one or more pharmaceutically acceptable carriers.

11. A method according to claim 10 wherein each of $R_1$ and $R_2$ is hydrogen; and each of $R_3$ and $R_4$ is independently hydrogen, alkyl of 1 to 4 carbon atoms, fluoro, chloro or trifluoromethyl.

12. A method according to claim 10 wherein each of $R_1$ and $R_2$ is hydrogen; and each of $R_3$ and $R_4$ is independently hydrogen, fluoro or chloro.

13. A method according to claim 10 wherein the compound is β-oxo-α-(2,4-difluorophenylcarbamoyl)-β-(2-pyrrolyl)-propionitrile or a pharmaceutically acceptable salt thereof as defined in said claim.

14. A method according to claim 10 wherein the compound is β-oxo-α-(4-chlorophenylcarbamoyl)-β-(2-pyrrolyl)-propionitrile or a pharmaceutically acceptable salt thereof as defined in said claim.

15. A method according to claim 10 wherein the compound is β-oxo-α-(3-trifluoromethylphenylcarbamoyl)-β-(2-pyrrolyl)-propionitrile or a pharmaceutically acceptable salt thereof as defined in said claim.

16. A method according to claim 10 wherein the compound is β-oxo-α-(phenylcarbamoyl)-β-(2-pyrrolyl)-propionitrile or a pharmaceutically acceptable salt thereof as defined in said claim.

17. A method according to claim 10 wherein the compound is β-oxo-α-(4-fluorophenylcarbamoyl)-β-(2-pyrrolyl)-propionitrile or a pharmaceutically acceptable salt thereof as defined in said claim.

* * * * *